US00PP10578P

United States Patent [19]

Hurlbut

[11] Patent Number: Plant 10,578

[45] Date of Patent: Sep. 1, 1998

[54] CHERRY TREE 'ANDY-G'S SON'

[76] Inventor: Robert L. Hurlbut, P.O. Box 368, Laton, Calif. 93242

[21] Appl. No.: 719,386

[22] Filed: Sep. 24, 1996

[51] Int. Cl.[6] ..... A01H 5/00

[52] U.S. Cl. ..... Plt./37

[58] Field of Search ..... Plt./37

[56] References Cited

U.S. PATENT DOCUMENTS

P.P. 9,787 1/1997 Otani ..... Plt./37

*Primary Examiner*—James R. Feyrer

*Attorney, Agent, or Firm*—Worrel & Worrel

[57] ABSTRACT

A new and distinct variety of cherry tree, *Prunus avium*, which produces fruit of uniformly large size and dark red skin coloration which are mature for harvesting and shipment about April 20 to about April 25 in the San Joaquin Valley of central California and which have a smooth, crisp flesh texture being firm in character at harvest.

1 Drawing Sheet

BACKGROUND OF THE NEW VARIETY

The present invention relates to a new and distinct variety of cherry tree, which will hereinafter be denominated varietally as the "Andy-G's Son" cherry tree and, more particularly, to such a cherry tree which produces fruit, which are mature for commercial harvesting and shipment approximately April 20 to April 25 in the San Joaquin Valley of central California.

In the development of new varieties of fruit trees, one objective which is rarely successfully achieved is that of finding varieties which can be grown in atypical climates. For example, in the case of cherry trees, most commercially successful varieties must be grown in comparatively cooler climates than that of the San Joaquin Valley of central California. Those cherry tree varieties which are grown in such warm climates typically have somewhat less than attractive characteristics such as, in the case of the fruit, comparatively small size, deficient flavor, poor bearing, a pronounced tendency to crack, susceptibility to pests and the like. Such characteristics, of course, detract from the commercial utility of the varieties thereby significantly limiting their usage and, to a certain degree, the development of other varieties.

With this in mind, it is very rare to find a variety of cherry tree which is both tolerant of warm climates while possessing commercially attractive characteristics such as fruit of uniformly large size, good flavor, high skin coloration, crisp firm flesh texture and regularity of bearing. The cherry tree of the subject invention appears to be such a new variety.

Origin and Asexual Reproduction of the New Variety

The present variety of cherry tree hereof was discovered by the inventor in his orchard which is located near Laton in the San Joaquin Valley of central California. The inventor discovered the new variety as a whole tree sport of the "Early Burlat" cherry tree (Unpatented) in 1988. The first fruit seen on this sport was in 1992 and no bloom on the parent tree was noticed prior to 1992. In early March of 1992, the sport set buds, blossomed and bore fruit before the "Early Burlatt" cherry trees which were planted in the orchard at the same time.

Due to the early production of fruit by sport of the new variety, graft wood was collected and trees were grafted.

More specifically, in 1993, twenty-five trees were Fall budded to the new variety. These asexually reproduced trees were set out in an orchard test block located near Laton in the San Joaquin Valley of central California in early 1995. The first blossoms and a few fruit of the asexually reproduced trees were observed in 1995. The asexually reproduced trees have continuously been observed since then and have been found in all respects to be identical to the parent sport of the new variety. The parent and asexually reproduced trees of the new variety were, in all instances, found to flower and bear fruit approximately five (5) to seven (7) days earlier than the "Early Burlatt" cherry trees.

SUMMARY OF THE NEW VARIETY

The cherry tree of the new variety is characterized by its vigorous growth under the climatic conditions prevailing in the San Joaquin Valley of central California. While the new variety appears to require pollination from other varieties, it consistently sets significantly better crops than other varieties of cherry tree under the same, growing conditions. Present test data indicates that the "Black Tartarian" and "Ranier" cherry tree cultivars may be suitable pollinators. However, the most recent test data also shows some evidence that the new variety of the subject invention might be somewhat self pollinating. The new variety produces a clingstone, or semi-clingstone, fruit of uniformly large size which has a deep red skin coloration and is ripe for commercial harvesting and shipment approximately April 20 to April 25 in the San Joaquin Valley of central California. The fruit of the new variety also appears to resist damage as a result of inopportune climatic conditions. For example, in other cherry tree varieties, rain occurring after the appearance of the fruit caused cracking of the fruit in those varieties, but not in the case of the fruit of the subject variety.

The botanical characteristics of the new variety differ from the parent variety "Early Byrlatt" cherry tree primarily in that it is earlier to flower and the fruit to ripen, in that the flesh is slightly more firm, in that the skin a slightly deeper red in coloration and in that the flavor of the fruit has a slightly different flavor, which has been described in comparison as "refreshing."

BRIEF DESCRIPTION OF THE DRAWING

The accompanying drawing is a color photograph showing representative fruit of the new variety including a first in side elevation with the stem detached, a second in bottom plan view showing the apex thereof, a third in side elevation with the stem attached, a fourth in side elevation with the stem attached and showing the suture thereof, a fifth in top plan view showing the stem cavity with the stem attached, a sixth in side elevation with the stem attached, a seventh in top plan view showing the stem cavity with the stem detached, an eighth sectioned along its vertical axis and laid open to expose the stone in one section and the stone cavity in the other section, and a ninih sectioned along its horizontal axis and laid open to expose the stone cavity in one section and the stone in the other section; three dry stones; and foliage, all of the subject variety.

DETAILED DESCRIPTION

Referring more specifically to the botanical details of this new and distinct variety of cherry tree, the following has been observed under the ecological conditions prevailing at the orchard of origin located in the central San Joaquin Valley of California. All major color code designations are by reference to the *Inter-Society Color Council, National Bureau of Standards.* Common color names are also occasionally employed.

Tree

Generally:

*Size.*—Normal for a cherry tree and dependant upon pruning. The general size and shape of the tree of the subject variety may most accurately be identified as "upright and spreading." The basic size and shape of the tree of the new variety are the same as the "Early Burlatt" and "Bing" cherry trees.

*Vigor.*—Vigorous.

*Figure.*—Normal for a cherry tree, depending on pruning and shaping.

*Productivity.*—Good.

*Regularity of Bearing.*—Seems to bear well every year, but may need more pollen.

Trunk:

*Size—diameter.*—Length—Normal for a cherry tree, depending on pruning and shaping.

*Surface texture.*—Normal rough.

*Surface texture—color.*—Gray brown (63 L.Br Gy).

*Lenticels—numbers.*—10 to 15 per square inch.

*Lenticels—size length.*—¼ inch (6.35 mm).

*Lenticels color.*—Bright brown (55. S.Br).

Branches:

*Size.*—Normal for a cherry tree, depending on pruning.

*Surface texture.*—Normal rough. The same as the trunk.

*Color—one year or older wood.*—Gray Brown (63 L.Br. Gy).

*Lenticels—Numbers.*—10 to 15 per square inch.

*Lenticels—color.*—Bright brown (55. S.Br). The same as the trunk.

Leaves

Size:

*Generally.*—Large for a cherry tree.

*Average length.*—5½ inches (139.7 mm) to 7¾ inches (196.85 mm).

*Average width.*—3 inches (76.2 mm) to 3⅜ inches (85.725 mm).

Shape: Lanceolate.

Color:

*Upwardly disposed surface.*—Dark green (126-D.ol.G).

*Downwardly disposed surface.*—Light green (127 gy.ol G).

Marginal form:

*Generally.*—Serrate.

Glandular characteristics: One pair base of leaf, reniform.

Gland:

*Color.*—Dark red (16 d.Red).

Petiole:

*Length.*—2 inches (50.8 mm).

*Width.*—3/32 inch (2.382 mm).

*Color.*—Upwardly disposed surface—Red (17 v.d. Red). Downwardly disposed surface—Green (136 m.y. Gr).

Stipules: Foliaceous, as shown.

Flowers

Flower Buds:

*Generally.*—This information taken as color starting to show at apex of flower bud. The flower buds are found in clusters on fruit spurs. There are 3 to 5 clusters of buds on each fruit spur.

*Size—length.*—5/16 inch (7.938 mm).

*Size*—diameter.—3/16 inch (4.763 mm).

*Shape.*—Elongated.

*Petiole length.*—3/16 inch (4.763 mm).

*Petiole—color.*—Light green (120 m.y.G).

Flowers:

*Generally.*—Like the buds, the flowers are found in clusters on fruit spurs. The flowers of the new variety are thought to require pollinators. The "Black Tartarian" and "Rainer" cherry trees have initially been identified as suitable pollinators. However, some evidence indicates that the new variety of the subject invention might be somewhat self pollinating.

Date of bloom: Approximately March 10 to March 17 at Kingsburg in the central San Joaquin Valley of California.

Size:

*Petal—length.*—⅝ (15.875 mm).

*Petal—Width.*—11/16 inch (17.463 mm).

Shape: Slightly elongated.

Petals:

*Color.*—White (263 white).

Petiole:

*Length.*—5/16 inch (7.938 mm).

*Diameter.*—1/16 inch (1.588 mm).

Fruit

Maturity When Described: Ripe for commercial harvesting and shipment approximately April 20 to April 25 near the Kingsburg and Selma areas in the central San Joaquin Valley of California.

Size:

*Uniformity.*—Good.

*Average diameter.*—1 inch (25.4 mm) to 1⅛ inches (28.575 mm).

*Average diameter on suture line.*—Approximately ⅞ inch (22.225 mm).

Shape:

*Generally.*—The fruit has a recessed suture line, giving it a slightly flat look.

Suture:

*Generally.*—Slightly recessed.

*Length.*—Approximately ⅞ inch (22.225 mm) from stem cavity to apex area.

Stem cavity:

*Shape.*—rounded.

*Width.*—¼ inch (6.35 mm).

*Depth.*—1/16 inch (1.588 mm).

Base: Almost flat in appearance, but is slightly rounded.

Apex:

*Shape.*—Almost flat in appearance but slightly rounded.

Pistil point: None, slightly recessed.

Stem:

*Length.*—⅝ (15.875 mm) to 1½ inches (38.1 mm).

*Width.*—1/16 inch (1.588 mm).

Skin:

*Thickness.*—Approximately 1/64 inch (397 mm).

*Texture.*—Very smooth.

*Tendency to crack.*—None.

*Color.*—Uniform, dark red (13 v.deep.Red).

Flesh:

*Flesh color.*—Mostly red (red—13 deep Red) with some white marks between skin and pit (263 white).

*Firmness.*—More firm than the "Early Burlatt" cherry tree.

*Surface of pit well.*—Almost smooth.

*Color of pit well.*—Very dark red (17 v.d. Red).

*Juice production.*—Very juicy.

*Flavor.*—Slightly tart but crisp and good. The flavor is slightly different than that of the fruit of the "Early Burlatt" cherry tree and has been described as "refreshing."

*Aroma.*—Slight.

*Texture.*—Smooth, crisp.

*Fibers.*—None, or few.

*Ripening.*—Even.

*Eating quality.*—Good.

Stone:

*Attachment.*—Cling, or semi-clingstone fruit.

*Fibers.*—None.

*Size—length.*—⅜ inch (9.525 mm).

*Size—width.*—⅜ inch (9.525 mm).

*Size—thickness.*—¼ inch (6.35 mm).

*Form—generally.*—Slightly flat.

*Color—dry.*—Light yellow (89 p.y.).

*Base—shape.*—Very small elongated, ⅛ inch (3.175 mm).

*Sides—generally.*—Smooth.

*Ridges.*—None.

Use: Fresh market.

Keeping quality: Holds well in cold storage. Seems to have a good shelf life.

Shipping and handling qualities: Due to firm nature at harvest, will ship well.

Although the new variety of cherry tree of the subject invention possesses the described characteristics noted above as a result of the growing conditions prevailing near Kingsburg and Selma in the central San Joaquin Valley of California, it is to be understood that variations of the usual magnitude and characteristics incident to changes in growing conditions, irrigation, fertilization, pruning, pest control, climatic variation, seasonal variation and the like are to be expected.

Having thus described and illustrated my new variety of cherry tree, what I claim as new and desire to be secured by plant letters patent is:

1. A new and distinct variety of cherry tree substantially as illustrated and described which is a sport of the "Early Burlatt" cherry tree and which produces fruit of uniformly large size which are mature for commercial harvesting and shipment approximately April 20 to April 25 in the San Joaquin Valley of central California and which have a dark red skin coloration.

* * * * *

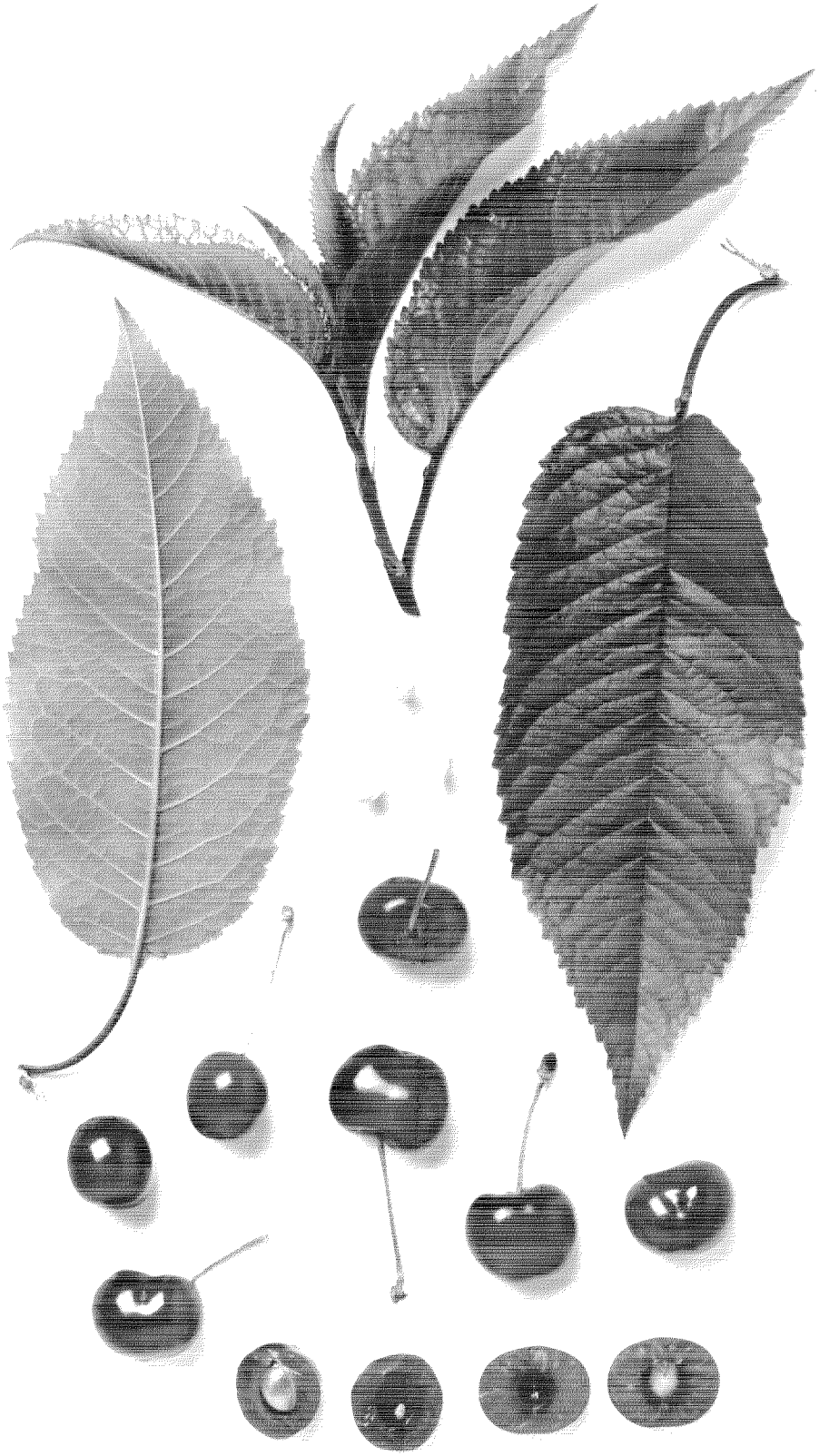

UNITED STATES PATENT AND TRADEMARK OFFICE

CERTIFICATE OF CORRECTION

PATENT NO. : Plant 10, 578

DATED : September 1, 1998

INVENTOR(S) : ROBERT L. HURLBUT

It is certified that error appears in the above-identified patent and that said Letters Patent is hereby corrected as shown below:

Column 1, line 39, delete "Early Burlat", and substitute ---"Early Burlatt"---.

Column 2, line 21, delete the "." between "same" and "growing".

Column 2, line 37, delete "Early Byrlatt", and substitute ---"Early Burlatt"---.

Column 3, line 10, delete "ninih", and substitute ---ninth---.

Column 5, line 18, delete "(397 mm).", and substitute ---(.397 mm).---.

Signed and Sealed this

Eighth Day of February, 2000

*Attest:*

*Attesting Officer*

Q. TODD DICKINSON

*Commissioner of Patents and Trademarks*